(12) United States Patent
Öhrlund et al.

(10) Patent No.: US 11,896,737 B2
(45) Date of Patent: *Feb. 13, 2024

(54) INJECTABLE GEL PRODUCT

(71) Applicant: Galderma Holding SA, Zug (CH)

(72) Inventors: Åke Öhrlund, Uppsala (SE); Morgan Karlsson, Knivsta (SE)

(73) Assignee: Galderma Holding SA, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/857,925

(22) Filed: Jul. 5, 2022

(65) Prior Publication Data

US 2022/0401625 A1 Dec. 22, 2022

Related U.S. Application Data

(63) Continuation of application No. 16/907,132, filed on Jun. 19, 2020, now Pat. No. 11,389,567, which is a continuation of application No. PCT/EP2018/085504, filed on Dec. 18, 2018.

(30) Foreign Application Priority Data

Dec. 22, 2017 (EP) ..................... 17210247

(51) Int. Cl.
| | | |
|---|---|---|
| A61L 27/48 | (2006.01) | |
| A61L 27/20 | (2006.01) | |
| A61L 27/26 | (2006.01) | |
| A61L 27/52 | (2006.01) | |
| C08B 37/00 | (2006.01) | |
| C08J 3/075 | (2006.01) | |
| C08J 3/12 | (2006.01) | |
| C08J 3/24 | (2006.01) | |
| C08L 5/08 | (2006.01) | |

(52) U.S. Cl.
CPC .............. *A61L 27/48* (2013.01); *A61L 27/20* (2013.01); *A61L 27/26* (2013.01); *A61L 27/52* (2013.01); *C08B 37/0063* (2013.01); *C08J 3/075* (2013.01); *C08J 3/126* (2013.01); *C08J 3/245* (2013.01); *C08L 5/08* (2013.01); *A61L 2400/06* (2013.01); *A61L 2430/34* (2013.01); *C08L 2203/02* (2013.01); *C08L 2205/025* (2013.01); *C08L 2207/53* (2013.01); *C08L 2312/00* (2013.01)

(58) Field of Classification Search
None
See application file for complete search history.

(56) References Cited

U.S. PATENT DOCUMENTS

| | | |
|---|---|---|
| 2007/0196426 A1 | 8/2007 | Hermitte et al. |
| 2010/0120911 A1 | 5/2010 | Majeed et al. |
| 2012/0190644 A1 | 7/2012 | D'Este et al. |
| 2016/0143943 A1 | 5/2016 | Ohno et al. |
| 2017/0143870 A1 | 5/2017 | Linko et al. |
| 2019/0023812 A1 | 1/2019 | Mojarradi et al. |

FOREIGN PATENT DOCUMENTS

| | | |
|---|---|---|
| CN | 103181902 A | 7/2013 |
| CN | 106589424 A | 4/2017 |
| EP | 0 466 300 | 1/1992 |
| EP | 2 011 816 A1 | 1/2009 |
| WO | WO-2011/086458 | 7/2011 |
| WO | WO-2017/114864 | 7/2017 |
| WO | WO-2017/114867 A1 | 7/2017 |

OTHER PUBLICATIONS

A. Tezel, G.H. Fredrickson. "The science of hyaluronic acid dermal fillers," Journal of Cosmetic and Laser Therapy, 2008, 10(1), pp. 35-42.
International Search Report dated Mar. 26, 2019 received in corresponding International Application No. PCT/EP2018/085504 (4 pages).
Khunmanee, Sureerat; et al., "Crosslinking method of hyaluronic-based hydrogel for biomedical applications." Journal of Tissue Engineering, 2017 (8), pp. 1-16, Published online Sep. 6, 2017.
Rohrich, Rod J., et al., "The Role of Hyaluronic Acid Fillers (Restylane) in Facial Cosmetic Surgery: Review and Technical Considerations," Plastic and Reconstructive Surgery, vol. 120, No. Supplement 1, Nov. 1, 2007, pp. 41S-54S, XP055480385, DOI:10.1097/01.prs.0000248794.63898.
S.C. Choi et al. "Modulation of biomechanical properties of hyaluronic acid hydrogels by crosslinking agents," Journal of Biomedical Materials Research Part A, 2015, 103(9), pp. 3072-3080.

*Primary Examiner* — Dale R Miller
(74) *Attorney, Agent, or Firm* — Sunit Talapatra; Foley & Lardner LLP (57) ABSTRACT

A method of producing an injectable gel product is provided, comprising (a) cross-linking a first glycosaminoglycan (GAG) with a first crosslinking agent to produce a gel, wherein the charging ratio of crosslinking agent to disaccharide unit is below 0.15; (b) preparing particles of the gel; (c) mixing the glycosaminoglycan (GAG) gel particles with a second GAG to provide a mixture; (d) cross-linking the mixture with a second crosslinking agent to obtain cross-linking between the GAGs of the second, outer phase, thereby providing a gel having a first, inner phase of the cross-linked GAG gel particles, embedded in a gel of the second GAG outer phase; and (e) preparing injectable particles, each such particle containing a plurality of the cross-linked GAG gel particles of the first, inner phase. An injectable gel product, an aqueous composition, and a pre-filled syringe as also provided.

35 Claims, 6 Drawing Sheets

INJECTABLE GEL PRODUCT

CROSS REFERENCE TO RELATED APPLICATIONS

This application is a continuation of U.S. patent application Ser. No. 16/907,132 filed Jun. 19, 2020, which application is a continuation of International Application No. PCT/EP2018/085504 filed Dec. 18, 2018, which claims the benefit of and priority to European Application No. 17210247.7 filed Dec. 22, 2017, both of which are hereby incorporated by reference herein in their entireties.

TECHNICAL FIELD OF THE INVENTION

The present invention relates to the field of polysaccharide gels. More specifically, the present invention relates to injectable gel products for use in cosmetic surgery.

BACKGROUND TO THE INVENTION

One of the most widely used biocompatible polymers for medical use is hyaluronic acid. It is a naturally occurring polysaccharide belonging to the group of glycosaminoglycans (GAGs). Hyaluronic acid (HA) and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

When used as an injectable filler, firm, densely crosslinked materials are often considered to have a stronger clinical effect, denoted "lifting capacity". It is also suggested that these materials may have a better longevity in the tissue. At the same time, very firm materials are suspected to sometimes give rise to unwanted tissue reactions, such as foreign body rejections, whereas softer materials are thought of as less problematic in this sense.

EP 466 300 A2 discloses a two-phase gel slurry in which the first phase comprises swollen polymeric gel particles dispersed in a second phase of a viscoelastic solution of a polymer.

US 2007/0196426 A1 discloses a crosslinked gel comprising a number of strongly crosslinked hubs interconnected by a gel which is less and less crosslinked, i.e. a gel in which the quantity of crosslinkage decreases progressively.

US 2016/0143943 A1 discloses core-shell HA gel particles with gradually increasing swelling capacity from the center to the surface.

EP 02011816 A1 discloses a co-crosslinked injectable gel having highly crosslinked gel particles bonded to a slightly crosslinked gel. The object is to provide a double action after injection; a first immediate filling and, in a second stage, when the slightly crosslinked gel is biodegraded in the tissues, a fibroblastic reactivation phenomenon following a mild foreign body reaction to the highly crosslinked particles.

SUMMARY OF THE INVENTION

Glycosaminoglycans filler materials, such as hyaluronic acid, are composed of small particles in order to allow injection through a thin needle. The inventors have found that simply mixing a firm and a soft filler material for injection will not provide a dual functionality in vivo since the particles will distribute and separate from each other to some extent upon injection into the tissue. Thus, when using an injectable material composed of a mix of firm and soft particles, tissue may immediately be subjected to the firm particles upon injection since the soft and hard particles separate and end up at different locations.

It is an object of the present invention to improve the lifting capacity of a filler material. For this and other objects that will be evident to a person skilled in the art from the following disclosure, the present invention provides according to a first aspect an injectable gel product comprising a first, inner phase of a plurality of cross-linked glycosaminoglycan (GAG) gel particles embedded in a second, outer phase of a cross-linked glycosaminoglycan (GAG) gel;

wherein the second, outer phase is in the form of particles;
wherein the Degree of Modification (MoD) of the gel of the first, inner phase is 0.15 or lower, and
wherein the MoD of the gel of the second, outer phase is lower than the MoD of the gel of the first, inner phase, and wherein
the MoD is the molar amount of bound cross-linking agent(s) relative to the total molar amount of repeating GAG disaccharide units.

The first aspect of the invention is based on the insight that in the injectable gel product, each particle will present itself as a soft material to the tissue, regardless of the distribution of particles in the tissue, thereby causing less tissue reactions. As the softer outer phase degrades over time, the inner phase will degrade to a lesser extent. With time, the outer phase is degraded to such a degree that it is dissolved and transported away from the injection site by tissue fluids. Since the initially inner and more firm phase material will have degraded into a softer material during this time, the material left at the injection site will be softer than the inner phase material was initially. This allows for the embedded material to provide a second period of functioning in the tissue, now with a reduced firmness for less tissue reaction. In other words, by selecting the firmness of the inner gel and the outer gel so that the outer gel is softer, the tissue may first be subjected to the outer softer gel but as this gel is slowly degraded, the tissue is eventually subjected to the initially firmer inner gel that has become softer during degradation of the outer gel, i.e. the inner gel has been allowed to swell in vivo before the tissue is in direct contact with the inner gel.

Furthermore, the injectable gel product may be prepared so that the tissue is subjected to a gel with similar properties, e.g. in terms of swelling or firmness, during longer periods of time. It may thus be desirable in certain applications that the exposed inner gel, after degradation of the outer gel, is as soft as the initial outer gel. However, in other applications, the exposed inner gel does not have to be as soft as the initial outer gel. Since the exposure of the inner gel will be greatly delayed and happen over a long time, the tissue reaction may be much weaker than it would be when directly injecting a firm gel.

The present invention further provides according to a second aspect a method of producing an injectable gel product, comprising the steps of:

a) cross-linking a first glycosaminoglycan (GAG) with a first crosslinking agent to produce a gel, wherein the charging ratio of crosslinking agent to disaccharide unit is below 0.15;
b) preparing particles of the gel from step a);
c) mixing the glycosaminoglycan (GAG) gel particles of step b) with a second glycosaminoglycan (GAG) to provide a mixture;

d) cross-linking the mixture of step c) with a second crosslinking agent to obtain cross-linking between the glycosaminoglycans (GAGs) of the second, outer phase, thereby providing a gel having a first, inner phase of the cross-linked glycosaminoglycan (GAG) gel particles, embedded in a gel of the second, outer phase comprising the second glycosaminoglycan (GAG); and e) preparing injectable particles of the gel from step d), each such particle containing a plurality of the cross-linked GAG gel particles of the first, inner phase.

As a third aspect of the invention, there is provided an aqueous composition comprising an injectable gel product according to the first aspect of the invention above and optionally a buffering agent.

Further, as a fourth aspect of the invention, there is provided a pre-filled syringe, which is pre-filled with an injectable gel product according to the first aspect of the invention above and then sterilized, or pre-filled with a sterilized aqueous composition according to the third aspect of the invention.

DETAILED DESCRIPTION OF THE INVENTION

As a first aspect of the invention, there is provided an injectable gel product comprising a first, inner phase of a plurality of cross-linked glycosaminoglycan (GAG) gel particles embedded in a second, outer phase of a cross-linked glycosaminoglycan (GAG) gel;

wherein the second, outer phase is in the form of particles;

wherein the Degree of Modification (MoD) of the gel of the first, inner phase is 0.15 or lower, and wherein the MoD of the gel of the second, outer phase is lower than the MoD of the gel of the first, inner phase, and wherein the MoD is the molar amount of bound cross-linking agent(s) relative to the total molar amount of repeating GAG disaccharide units.

An injectable gel product refers to the gel being capable to flow and be injected through a syringe, such as a through a syringe having a needle of fine diameter as generally required in cosmetic surgery. The needle may be of the type 27 gauge. Thus, the injectable gel product may be ready to be packaged in a syringe.

The injectable gel product may be regarded as biphasic, i.e. comprising a first, inner phase comprising the plurality of gel particles embedded in a second, outer gel phase. The inner phase may have a higher concentration of GAGs, may be more firm and/or have a higher degree of cross-linking.

The injectable gel product may also be cohesive or exhibit cohesivity, e.g. as defined in WO 11086458 A1.

A glycosaminoglycan (GAG) is a negatively charged heteropolysaccharide chain which have a capacity to absorb large amounts of water. The GAG may for example be sulfated or non-sulfated glycosaminoglycans such as hyaluronan, chondroitin sulphate, heparan sulphate, heparosan, heparin, dermatan sulphate and keratan sulphate. In some embodiments the GAG is hyaluronic acid, chondroitin or chondroitin sulfate.

The gel of the inner phase and/or the outer phase may be a hydrogel. That is, they may be regarded as a water-insoluble, but substantially dilute, cross-linked systems of GAG molecules when subjected to a liquid, typically an aqueous liquid.

The gel of the first inner phase and the gel of the second outer phase are cross-linked. The gels thus comprise a continuous shaped network of GAG molecules which is held together by the covalent cross-links, physical entangling of the GAG chains and various interactions, such as hydrogen bonding, van der Waals forces and electrostatic interactions.

The Degree of Modification (MoD) is a measure of the degree of cross-linking. MoD is expressed as mole/mole, a dimensionless number, or mole %. MoD describes the amount of cross-linking agent(s) that is bound to the GAG, i.e. molar amount of bound cross-linking agent(s) relative to the total molar amount of repeating GAG disaccharide units. MoD thus reflects to what degree the GAG has been chemically modified by cross-linking agent(s).

Another quantity for measuring the degree of cross-linking is the charging ratio, i.e. the ratio between the number of crosslinking agents added to the reaction vessel and the total number of disaccharide units added to the reaction vessel when performing the cross-linking reaction.

As an example, the degree of cross-linking of the gel product may be such that the charging ratio is less than 0.1, preferably less than or equal to 0.02, when preparing the gels of both the first, inner phase and the second, outer phase.

The gel of the first inner phase and the gel of the second outer phase are further in the form of particles, i.e. in the form of fragments that may have any type of shape, regular or irregular. The sizes may be non-uniform, i.e. the gel product may comprise particles of different sizes. Furthermore, the gel particles of the outer phase comprise a plurality of inner gel particles. In other words, the particle size of the outer gel is larger than the particle size of the inner gel.

The gel particles of the second outer phase may have a size that is 0.1 mm.

The first aspect of the invention is based on the insight that embedding a densely crosslinked, and therefore firm, material into a lightly crosslinked, and therefore soft, material may give stronger lifting capacity in the tissue. However, the inventors have found that having a MoD of less than 0.15 in the gel of the inner phase and an even lower MoD in the gel of the outer phase is advantageous in that it makes the combination gel ideal for injection. The gel product of the present invention is thus soft enough to cause little tissue reactions upon injection.

With time, the soft material is degraded to such a degree that it is dissolved and transported away from the injection site by tissue fluids. Due to the MoD of less than 0.15, the initially firmer inner material will have degraded into a softer material during this time. Thus, the material left at the injection site will be softer than the firm material was initially. This allows for the embedded material to provide a second period of functioning in the tissue, now with a reduced firmness for less tissue reaction. In other words, due to the MoD of less than 0.15 in the gel of the inner phase and an even lower MoD in the gel of the outer phase, the tissue is exposed to a soft gel over a long period of time.

DESCRIPTION OF EMBODIMENTS

It is to be understood that the first, inner phase of the plurality of cross-linked glycosaminoglycan (GAG) gel particles themselves may comprise further phases, such as smaller particles embedded within the first, inner phase of the plurality of cross-linked glycosaminoglycan (GAG) gel particles, and such smaller particles may have even smaller particles embedded within, and so on.

In embodiments, the Degree of Modification (MoD) of the gel of the first, inner phase is 0.10 or lower, such as 0.05 or lower, such as 0.02 or lower.

In embodiments, the Degree of Modification (MoD) of the gel of the second, outer phase is 0.10 or lower. Gels with such a softness may be suitable for contact with tissue after injection.

However, the MoD of the second outer phase may be above 0.05, such as above 0.05, but less than the MoD of the gel of the inner phase. As an example, the MoD of the gel of the second, outer phase may be between 0.08 and 0.095. Gels having such a MoD have been found to be firm enough to hold together as a cohesive gel but still be perceived as soft upon injection.

A relevant physical property of a cross-linked GAG gel product is the volume of liquid that the gel can absorb and is related to the structural stability of the gel, often referred to as gel strength or firmness. Traditional expressions for the liquid absorption are swelling, swelling capacity, liquid retention capacity, swelling degree, swelling factor, maximum liquid uptake and maximum swelling. Throughout this text, the term swelling factor (SwF) will be used.

When the gel is subjected to non-precipitating conditions, it is possible to determine its swelling factor, or inversely its minimum concentration ($C_{min}$), i.e. the GAG concentration when the gel product is fully swollen. Further addition of liquid will not dilute the gel further, i.e. the gel cannot be indefinitely diluted like a solution of free molecules. Firmer (low-swelling) gels are generally expected to have a longer half-life in vivo than softer (high-swelling) gels.

In embodiments, the Swelling factor (SwF) of the gel of the second, outer phase is above 3.0, such as above 4.0. Such a gel may be perceived as soft for the tissue.

However, the swelling factor of the gel of the second, outer phase may still be below 10.0, i.e. between 3.0 and 10.0, such as between 3.0 and 5.0. A gel having such a swelling factor may be soft enough to be perceived as soft, but be firm enough to retain a plurality of the inner gel particles embedded in the gel during manufacture, such as after Particle Size Reduction (PSR) of the outer gel. PSR is a process in which a gel is pushed through a grid, thereby breaking the gel into particles having an average particles size corresponding to the through holes of the grid.

In embodiments, the gels of the first, inner phase and the second, outer phase are cross-linked to each other.

Thus, the gels may be cross-lined to each other so as to form a single, cohesive gel, in contrast to having the inner gel particles dispersed in the outer gel. The cross-links between the inner and outer gels may be performed while crosslinking the outer gel. This may be advantageous in that it may prevent inner gel particles from separating from the outer gel before the outer gel has been fully dissolved after injection.

In embodiments, the Degree of Modification (MoD) is substantially homogenous throughout the second, outer phase and substantially homogenous throughout the first, inner phase.

Thus, the degree of cross-linking may be substantially homogeneous in both gel phases, such as constant when seen in a direction from the center of the gel and outwards. This is thus in contrast to a gel in which the degree of crosslinking varies within the gel.

The outer gel particles may comprise at least five inner gel particles, such as at least ten inner gel particles, such as at least twenty inner gel particles.

In embodiments, the outer gel particle size is at least three times the size of an inner particle size.

Furthermore, the inner particles may have an average size that is less than 0.200 mm.

In embodiments, the dry weight content of the cross-linked glycosaminoglycan (GAG) of the first, inner phase is at least 25% of the total dry weight content of glycosaminoglycans (GAGs) in the inner and outer phase, such as at least 50% of the total dry weight content of glycosaminoglycans (GAGs) in the inner and outer phase.

Such gels may be soft enough to provide an initial softness in vivo but have high enough inner particle content to provide a second function once the outer gel has dissolved.

As an example, the dry weight content of the cross-linked glycosaminoglycan (GAG) of the first, inner phase may be at least 60% of the total dry weight content of glycosaminoglycans (GAGs) in the inner and outer phase.

As a further example, the dry weight content of the cross-linked glycosaminoglycan (GAG) of the first, inner phase may be between 65% and 95% of the total dry weight content of glycosaminoglycans (GAGs) in the inner and outer phase.

In embodiments, the glycosaminoglycan (GAG) is hyaluronic acid.

Unless otherwise provided, the term "hyaluronic acid" encompasses all variants and combinations of variants of hyaluronic acid, or hyaluronan, of various chain lengths and charge states, as well as with various chemical modifications That is, the term also encompasses the various hyaluronate salts of hyaluronic acid, such as sodium hyaluronate. Various modifications of the hyaluronic acid are also encompassed by the term, such as oxidation, e.g. oxidation of $CH_2OH$ groups to COOH; periodate oxidation of vicinal hydroxyl groups, optionally followed by reduction or imine formation etc; reduction, e.g. reduction of COOH to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to hyaluronic acid; and deacetylation.

As an example, the hyaluronic acid may be a chemically unmodified hyaluronic acid or hyaluronate salt, preferably sodium hyaluronate, having an average molecular weight in the range of 0.1-10 MDa, preferably 0.8-5 MDa, more preferably 0.8-1.2 MDa. It is preferred that the hyaluronic acid is obtained from non-animal origin, preferably bacteria.

In some embodiments, the cross-linking of the inner and/or the outer gel is performed using one or more polyfunctional cross-linking agent(s) individually selected from the group consisting of divinyl sulfone, multiepoxides and diepoxides. In certain embodiments, the polyfunctional cross-linking agent(s) is individually selected from the group consisting of 1,4-butanediol diglycidyl ether (BDDE), 1,2-ethanediol diglycidyl ether (EDDE) and diepoxyoctane. In specific embodiments, the polyfunctional cross-linking agent is 1,4-butanediol diglycidyl ether (BDDE).

Thus, in embodiments, the crosslinking is ether bonds.

In embodiments, crosslinking of the glycosaminoglycan is achieved by amide coupling of glycosaminoglycan molecules. The amide coupling may be performed using a di- or multinucleophile functional crosslinker.

Amide coupling using a di- or multiamine functional crosslinker together with a coupling agent is an attractive route for preparing crosslinked glycosaminoglycan molecules useful in the present invention.

Crosslinking can be achieved using a non-carbohydrate based di- or multinucleofile crosslinker, for example hexamethylenediamine (HMDA), or a carbohydrate based di- or multinucleofile crosslinker, for example diaminotrehalose (DATH) together with a glycosaminoglycan.

Thus, the crosslinker comprising at least two nucleophilic functional groups may for example be a non-carbohydrate based di- or multinucleophilic crosslinker or a carbohydrate based di- or multinucleophilic crosslinker.

A preferred group of di- or multinucleophile functional crosslinker includes homo- or heterobifunctional primary amines, hydrazines, hydrazides, carbazates, semi-carbazides, thiosemicarbazides, thiocarbazates and aminoxy.

The di- or multinucleophile functional di-, tri-, tetra-, and oligo-saccharides may be derived from nucleophile functional polysaccharides, such as chitobiose derived from chitin. The di- or multinucleophile functional di-, tri-, tetra-, and oligo-saccharides may also be di-, tri-, tetra-, and oligo-saccharides which have been modified by introduction of two or more nucleophile functional groups.

Carbohydrate based di- or multinucleophilic crosslinkers may be advantageous, since they provide a hydrogel product based entirely on carbohydrate type structures or derivatives thereof, which minimizes the disturbance of the crosslinking on the native properties of the glycosaminoglycans. The crosslinker itself can also contribute to maintained or increased properties of the hydrogel, for example when crosslinking with a structure that correlates to hyaluronic acid or when crosslinking with a structure with high water retention properties.

In embodiments, the di- or multinucleofile crosslinker is an at least partially deacetylated polysaccharide, i.e. an acetylated polysaccharide which has been at least partially deacetylated to provide a polysaccharide having free amine groups. An at least partially deacetylated glycosaminoglycan, can be crosslinked either alone or in combination with a second glycosaminoglycan, whereby the deacetylated glycosaminoglycan itself acts as the di- or multinucleofile crosslinker.

In embodiments of the first aspect of the invention, the glycosaminoglycan molecules of the first, inner phase and/or the glycosaminoglycan molecules of the second outer phase are covalently crosslinked via crosslinks comprising a spacer group selected from the group consisting of di-, tri-, tetra-, and oligosaccharides.

The crosslink typically consists of i) the spacer group and ii) the binding groups formed upon reaction of the functional groups of the crosslinker with the carboxylic acid groups on the GAG. The spacer group may for example comprise a hyaluronic acid tetrasaccharide, hyaluronic acid hexasaccharide, trehalose, lactose, maltose, sucrose, cellobiose or raffinose residue.

Crosslinking via crosslinkers comprising a spacer group selected from the group consisting of di-, tri-, tetra-, and oligosaccharides provides a hydrogel product based entirely on carbohydrate type structures or derivatives thereof, which minimizes the disturbance of the crosslinking on the native properties of the glycosaminoglycans. The di-, tri-, tetra-, or oligosaccharide is preferably well defined in terms of structure and molecular weight. Preferably the spacer is selected from one specific di-, tri-, tetra-, or oligosaccharide structure. Preferably, the di-, tri-, tetra-, or oligosaccharide is mono-disperse or has a narrow molecular weight distribution. Using well defined di-, tri-, tetra-, or oligosaccharide based crosslinkers together with a highly efficient condensation reaction allows the product to be assembled in a controlled fashion. The crosslinker itself can also contribute to maintained or increased properties of the hydrogel, for example when crosslinking with a structure that correlates to hyaluronic acid (e.g. diamino hyaluronic acid tetrasaccharide) or when crosslinking with a structure with high water retention properties (e.g. trehalose)

As an example, at least 75% of the crosslinks may comprise a spacer group selected from the group consisting of di-, tri-, tetra-, and oligosaccharides.

Further, the spacer group may be a hyaluronic acid tetrasaccharide, hyaluronic acid hexasaccharide, trehalose, lactose, maltose, sucrose, cellobiose or raffinose residue.

Moreover, the spacer group may be selected from the group consisting of di-, tri- and tetrasaccharides.

In embodiments of the first aspect of the invention, at least 90% of the bonds between glycosaminoglycan molecules and crosslinks are amide bonds.

Furthermore, less than 5% of the bonds between glycosaminoglycan molecules and crosslinks may be ester bonds.

The first and/or second glycosaminoglycan may further be crosslinked using a peptide coupling reagent. Crosslinking using a peptide coupling agent is advantageous over many other common crosslinking methods (e.g. BDDE crosslinking) since it allows for crosslinking to be performed at neutral pH with minimal degradation of the glycosaminoglycan molecules.

According to some embodiments, the peptide coupling reagent is selected from the group consisting of triazine-based coupling reagents, carbodiimide coupling reagents, imidazolium-derived coupling reagents, Oxyma and COMU.

According to some embodiments, the peptide coupling reagent is a triazine-based coupling reagent. According to some embodiments, the triazine-based coupling reagent is selected from the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT). According to some embodiments, the triazine-based coupling reagent is DMTMM.

According to some embodiments, the peptide coupling reagent is a carbodiimide coupling reagent. According to some embodiments, the carbodiimide coupling reagent is N-(3-dimethylaminopropyl)-N'-ethylcarbodiimide (EDC) combined with N-hydroxysuccinimide (NHS).

The injectable gel product may also comprise a portion of GAG molecules which are not crosslinked, i.e. not bound to a three-dimensional crosslinked GAG molecule network. However, it is preferred that at least 50% by weight, preferably at least 60% by weight, more preferably at least 70% by weight, and most preferably at least 80% by weight, of the GAG molecules injectable gel product form part of a crosslinked GAG molecule network.

As a second aspect of the invention, there is provided a method of producing an injectable gel product, comprising the steps of:
a) cross-linking a first glycosaminoglycan (GAG) with a first crosslinking agent to produce a gel, wherein the charging ratio of crosslinking agent to disaccharide unit is below 0.15;
b) preparing particles of the gel from step a);
c) mixing the glycosaminoglycan (GAG) gel particles of step b) with a second glycosaminoglycan (GAG) to provide a mixture;
d) cross-linking the mixture of step c) with a second crosslinking agent to obtain cross-linking between the glycosaminoglycans (GAGs) of the second, outer phase, thereby providing a gel having a first, inner phase of the cross-linked glycosaminoglycan (GAG)

gel particles, embedded in a gel of the second, outer phase comprising the second glycosaminoglycan (GAG), and e) preparing injectable particles of the gel from step d), each such particle containing a plurality of the cross-linked GAG gel particles of the first, inner phase.

The terms and definitions used in relation to the second aspect of the invention are as discussed in relation to the first aspect above.

In embodiments, the injectable particles produced in step e) are a gel product as disclosed in relation to any embodiment of the first aspect above.

The method of the second aspect is advantageous in that it is a convenient process for producing a combination gel, i.e. for embedding a densely crosslinked, and therefore firm, material into a lightly crosslinked, and therefore soft, material. Such a combination gel may give stronger lifting capacity in the tissue. The inventors have found that having a charging ratio in step a) of below 0.15, i.e. when producing the "inner" GAG gel particles, and an even lower charging ratio in step d), i.e. when embedding the inner GAG gel particles in the outer matrix, facilitates the formation of a gel product that may give stronger lifting capacity in the tissue.

Further, the method of the second aspect of the invention is advantageous in that it allows for an effective process for producing the injectable gel-product, since low amounts of cross-linking agent may be used.

The steps of embedding already crosslinked particles within a gel that is subsequently crosslinked may be repeated for any number of times, such as at least two times or at least three times. Thus, step d) may further comprise preparing particles of the provided gel and these prepared particles may be used in a repeated step c) in which they are mixed with e.g. a third glycosaminoglycan (GAG) to provide a mixture, that is subsequently crosslinked in a repeated step d) to form a gel. Particles of this gel may yet again be mixed with further GAGs, and so on.do not check Thus, steps c) and d) may be repeated any number of times. The crosslinking agent used in the crosslinking steps may be as discussed in the first aspect of the invention above.

As an example, the crosslinking in step a) and/or step b) may result in ether bonds.

As a further example, the crosslinking in step a) and/or step b) may result in GAG molecules being covalently crosslinked via crosslinks comprising a spacer group selected from the group consisting of di-, tri-, tetra-, and oligosaccharides.

The crosslinking in step d) may be performed using the same crosslinking conditions as the crosslinking in step a). The charging ratio in step d) may be the same as in step a) or different.

Further, the crosslinking in step d) may be performed using the same crosslinking agent as in step a) or using a different crosslinking agent than the crosslinking agent used in step a). Consequently, the first and second crosslinking agents may be the same or different- Further, the cross-linking of steps a) and/or d) may be performed by an initial addition of cross-linking agent to increase the homogeneity of crosslinkage in the first and/or outer gel.

The charging ratio of step a) may be less than 0.10, such as less than 0.05.

As an example, the charging ratio of step a) may be between 0.002-0.10, such as between 0.005-0.10, such as between 0.005-0.05, such as between 0.005-0.03, such as between 0.01-0.3.

In embodiments, the charging ratio of crosslinking agent to disaccharide unit in step d) is less than 0.10, such as less than 0.05. The inventors have found that such a low charging ratio when producing the outer gel matrix may still provide a gel product with suitable degrading characteristics in situ.

In embodiments, the charging ratio of crosslinking agent to disaccharide unit in step d) is less than the charging ratio of step a).

In embodiments, the cross-linking of step d) further comprises obtaining cross-linking between the gels of the first, inner phase and the second, outer phase. Thus, the second crosslinking agent used in step d) may further aid in crosslinking the outer gel matrix to the embedded gel particles, and may thus aid in retaining the embedded gel particles within the gel when preparing the injectable particles in step e).

In embodiments, step c) comprises mixing the glycosaminoglycan (GAG) gel particles of step b) in dry state with the second glycosaminoglycan (GAG) in dry state. The gel particles in dry state may for example be in powder form or in the form of dry entangled strings. Mixing in dry state may be advantageous in that it provides for good mixing between the first and second GAGs, i.e. it provides for an even distribution of the gel particles of the first inner phase within the outer phase.

However, step c) may comprise first dissolving the glycosaminoglycan (GAG) gel particles of step b) and mixing the solution with a solution comprising the second glycosaminoglycan (GAG).

In embodiments, the step of preparing particles of step b) further comprises precipitating and drying said particles prepared of the gel of step a).

Precipitation of the inner gel particles is advantageous in that it further increases the possibilities of washing the gel particles of the first inner phase, e.g. to decrease the number of by-products, such as unreacted cross-linking agents. The precipitation in itself may act as a cleaning step; i.e. unwanted by-products may be separated from the gel particles during the actual precipitation.

Further, precipitation of the inner gel particles may make the inner gel particles more accessible for crosslinking agents during the second step of crosslinking, i.e. during step d). This means that lower amounts of crosslinking agent may be used in the second crosslinking step, i.e. precipitation increases the effective use of the crosslinking agents and thus increases the effectiveness of the whole method.

Moreover, a precipitated powder may be stored and therefore, the second crosslinking of step d) does not have to be performed immediately after the precipitation. Thus, step c) may be performed at least 1 hour after the precipitation, such as at least 5 hours, such as at least 10 hours, such as at least 24 hours, such as at least 48 hours after precipitation. Hence, a step of precipitating and drying the particles prepared of the gel of step a) increases the flexibility of the process.

Consequently, a step of precipitation is advantageous in that it allows for cleaning of the gel particles, the process becomes more flexible in that the two cross-linking steps may be divided in more distinct and separate crosslinking steps and the overall effectiveness of the process in increased due to the use of lower amounts of crosslinking agent.

In embodiments of the second aspect, the mixture of step c) contains at least 45% by dry weight of the GAG gel particles obtained in step b), such as at least 50% by dry weight of the GAG gel particles obtained in step b). Thus, the dry weight content of the cross-linked glycosaminoglycan (GAG) of the first, inner phase may be at least 50% of the total dry weight content of glycosaminoglycans (GAGs) in step c).

As an example, the mixture of step c) may contain at least 60% by dry weight of the GAG gel particles obtained in step b).

As a further example, the mixture of step c) may contain between 65% and 95% by dry weight of the GAG gel particles obtained in step b). Thus, the dry weight content of the cross-linked glycosaminoglycan (GAG) of the first, inner phase may be between 65% and 95% of the total dry weight content of glycosaminoglycans (GAGs) in the inner and outer phase.

As a third aspect of the invention, there is provided an aqueous composition comprising an injectable gel product according to any embodiment of the first aspect above and optionally a buffering agent.

The aqueous composition may be suitable for injection. The aqueous composition may typically contain a physiological salt buffer. The composition may further comprise other suitable additives, such as local anaesthetics (e.g. lidocaine hydrochloride), anti-inflammatory drugs, antibiotics, and other suitable supportive medications, e.g. bone growth factors or cells.

Administration of the injectable gel product or the aqueous composition may be performed in any suitable way, such as via injection from standard cannulae and needles of appropriate sizes or surgical insertion, e.g. in the case of administration of a film. The administration is performed where the soft tissue augmentation is desired, such as the chin, cheeks or elsewhere in the face or body.

Thus, as a fourth aspect of the invention there is provided a pre-filled syringe, which is pre-filled with a sterilized, injectable gel product according to any embodiment of the first aspect above or a sterilized aqueous composition according to the third aspect above.

The gel product may be kept in precipitated form in the syringe be brought to its non-precipitated form prior to injection or in the body following injection thereof.

The gel product may further be autoclavable, since this is the most convenient way of sterilising the final product. This allows for preparation of a sterilized, injectable gel product.

In certain embodiments, the injectable gel product or the aqueous composition according to the first and third aspects above are useful as a medicament or medical device in a medical or surgical method.

According to a further aspect, there is provided the use of an injectable gel product according to the first aspect above or the aqueous composition according to third aspect above in cosmetic or medical surgery. Put another way, there is provided an injectable gel product or an aqueous composition for use in cosmetic or medical surgery.

In some embodiments, the use is in cosmetic surgery selected from dermal filling and body contouring. In some other embodiments, the use is as a medicament in the treatment of, and/or in medical surgery selected from, dermal filling, body contouring, prevention of tissue adhesion, formation of channels, incontinence treatment, and orthopaedic applications.

According to one aspect, there is provided a method of treatment of a subject undergoing cosmetic or medical surgery, involving administration of an injectable gel product according to the first aspect above or the aqueous composition according to third aspect above to a subject in need thereof.

In certain embodiments, the subject is undergoing cosmetic surgery selected from dermal filling and body contouring. In certain other embodiments, the subject is undergoing medical surgery, or medical treatment, for a condition selected from dermal filling, body contouring, prevention of tissue adhesion, formation of channels, incontinence treatment, and orthopaedic applications.

The glycosaminoglycan may itself act as a crosslinker in a crosslinked gel, e.g. when a deacetylated glycosaminoglycan is used. In such cases, the Degree of Modification (MoD), which is a relevant property when using crosslinking agents other than the glycosaminoglycan itself, may correspond to the degree of deacetylation of the glycosaminoglycan. Thus, all embodiments and examples of MoD discussed in relation to the previous aspects above may also be relevant when the glycosaminoglycan itself acts as a crosslinker, but then as degree of deacetylation of the glycosaminoglycan.

Thus, as a general aspect of the present invention, there is provided an injectable gel product comprising a first, inner phase of a plurality of cross-linked glycosaminoglycan (GAG) gel particles embedded in a second, outer phase of a cross-linked glycosaminoglycan (GAG) gel;

wherein the second, outer phase is in the form of particles;

wherein maximum amount of crosslinkages relative to the total molar amount of repeating GAG disaccharide units of the gel of the first, inner phase is 0.15 or lower, and wherein the maximum amount of crosslinkages relative to the total molar amount of repeating GAG disaccharide units of the gel of the second, outer phase is lower than the maximum amount of crosslinkages relative to the total molar amount of repeating GAG disaccharide units of the gel of the first, inner phase.

The maximum amount of crosslinkages relative to the total molar amount of repeating GAG disaccharide units may for example be the MoD if a separate crosslinking agent other than the GAG itself is used for crosslinking or the degree of deacetylation if the GAG itself acts as the crosslinker. Furthermore, when using the glycosaminoglycan itself acts as a crosslinker in the crosslinked gel, the alternative aspects discussed below may become relevant. The terms and definitions used in relation to these alternative aspects are as discussed in relation to the previous aspects above.

Thus, as an alternative aspect of the present invention, there is provided an injectable gel product comprising a first, inner phase of a plurality of cross-linked glycosaminoglycan (GAG) gel particles embedded in a second, outer phase of a cross-linked glycosaminoglycan (GAG) gel;

wherein the second, outer phase is in the form of particles and wherein the glycosaminoglycan (GAG) of the first inner phase and/or the glycosaminoglycan (GAG) of the second outer phase comprises crosslinks in which the glycosaminoglycan itself acts as a di- or multinucleofile crosslinker.

In embodiments, the degree of deacetylation of the gel of the first, inner phase is 0.15 or lower, and wherein the degree of deacetylation of the gel of the second, outer phase is lower than the degree of deacetylation of the gel of the first, inner phase.

In an embodiment, only the glycosaminoglycan (GAG) of the first inner phase comprises crosslinks in which the glycosaminoglycan itself acts as a di- or multinucleofile crosslinker.

In an embodiment, only the glycosaminoglycan (GAG) of the second outer phase comprises crosslinks in which the glycosaminoglycan itself acts as a di- or multinucleofile crosslinker.

In an embodiment, the glycosaminoglycan (GAG) of the first inner phase and the glycosaminoglycan (GAG) of the second outer phase comprises crosslinks in which the glycosaminoglycan itself acts as a di- or multinucleofile crosslinker.

As an example, a deacetylated glycosaminoglycan itself may act as the di- or multinucleofile crosslinker.

Thus, the glycosaminoglycan itself acting as a di- or multinucleophilic crosslinker may be an at least partially deacetylated glycosaminoglycan, i.e. an acetylated glycosaminoglycan which has been at least partially deacetylated to provide a glycosaminoglycan having free amine groups. An at least partially deacetylated glycosaminoglycan can be crosslinked either alone or in combination with a second glycosaminoglycan, whereby the deacetylated glycosaminoglycan itself acts as the di- or multinucleophilic crosslinker.

As a further alternative aspect of the present invention, there is provided a method for producing an injectable gel product, comprising the steps of:
 a) cross-linking a first glycosaminoglycan (GAG) to produce a gel,
 b) preparing particles of the gel from step a);
 c) mixing the glycosaminoglycan (GAG) gel particles of step b) with a second glycosaminoglycan (GAG) to provide a mixture;
 d) cross-linking the mixture of step c) to obtain cross-linking between the glycosaminoglycans (GAGs) of the second, outer phase, thereby providing a gel having a first, inner phase of the cross-linked glycosaminoglycan (GAG) gel particles, embedded in a gel of the second, outer phase comprising the second glycosaminoglycan (GAG), and
 e) preparing injectable particles of the gel from step d), each such particle containing a plurality of the cross-linked GAG gel particles of the first, inner phase.

The crosslinking of step a) and/or step d) may be achieved using an at least partially deacetylated glycosaminoglycan, either alone or in combination with a second glycosaminoglycan, whereby the deacetylated glycosaminoglycan itself acts as the di- or multinucleofile crosslinker.

The degree of deacetylation of the first glycosaminoglycan in step a) may be below 0.15. The degree of deacetylation of the second glycosaminoglycan in step d) may be less than the degree of deacetylation of the first glycosaminoglycan.

By the term "at least partially deacetylated" as used herein regarding the glycosaminoglycan, it is meant a glycosaminoglycan comprising N-acetyl groups in which at least some of the N-acetyl groups have been cleaved off, resulting in the formation of free amine groups in the glycosaminoglycan. By "at least partially deacetylated" as used herein, we mean that a significant portion of the N-acetyl groups of the glycosaminoglycan, particularly at least 1%, preferably at least 2%, at least 3%, at least 4%, at least 5%, of the N-acetyl groups of the glycosaminoglycan have been converted to free amine groups. More preferably, at least 3% of the N-acetyl groups of the glycosaminoglycan have been converted to free amine groups.

According to some embodiments, the at least partially deacetylated glycosaminoglycan may have a degree of acetylation of less than 99%, preferably less than 98%, less than 97%, less than 97%, less than 96%, less than 95%, less than 94% or less than 93%.

The crosslinking of deacetylated glycosaminoglycan may be performed with the aid of a coupling agent, such as a peptide coupling reagent.

According to some embodiments, the peptide coupling reagent is selected from the group consisting of triazine-based coupling reagents, carbodiimide coupling reagents, imidazolium-derived coupling reagents, Oxyma and COMU.

According to some embodiments, the peptide coupling reagent is a triazine-based coupling reagent. According to some embodiments, the triazine-based coupling reagent is selected from the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT). According to some embodiments, the triazine-based coupling reagent is DMTMM.

According to some embodiments, the peptide coupling reagent is a carbodiimide coupling reagent. According to some embodiments, the carbodiimide coupling reagent is N-(3-dimethylaminopropyl)-N'-ethylcarbodiimide (EDC) combined with N-hydroxysuccinimide (NHS).

Consequently, step a) may comprise the sub steps:
 i) providing a solution comprising an at least partially deacetylated glycosaminoglycan and optionally a further glycosaminoglycan;
 ii) activating carboxyl groups on the at least partially deacetylated glycosaminoglycan and/or the optional further glycosaminoglycan with a coupling agent, to form activated glycosaminoglycans;
 iii) crosslinking the activated glycosaminoglycans via their activated carboxyl groups using amino groups of the at least partially deacetylated glycosaminoglycans to provide a gel of glycosaminoglycans crosslinked by amide bonds.

As a further example, the second glycosaminoglycan may be at least partially deacetylated glycosaminoglycan and step d) may comprise the sub steps
 i) activating carboxyl groups on the at least partially deacetylated second glycosaminoglycan with a coupling agent, to form activated glycosaminoglycans;
 ii) crosslinking the activated glycosaminoglycans via their activated carboxyl groups using amino groups of the at least partially deacetylated glycosaminoglycans to provide the second, outer phase comprising the second glycosaminoglycan (GAG) crosslinked by amide bonds.

In other embodiments, the crosslinked GAG is step a) and/or step d) is obtained by:
 1) crosslinking at least partially deacetylated GAG to partially deacetylated GAG in the presence of a coupling agent using free amine and carboxylic acid groups present in the at least partially deacetylated GAGs; or
 2) crosslinking at least partially deacetylated GAG to a non-deacetylated GAG in the presence of a coupling agent using free amine groups present in the at least partially deacetylated GAG and carboxylic acid groups present in the GAG.

In embodiments, the at least partially deacetylated glycosaminoglycan has a degree of acetylation of 99% or less, preferably 98% or less, preferably 97% or less, preferably 96% or less, preferably 95% or less, preferably 94% or less, preferably 93% or less, and a weight average molecular weight of 0.1 MDa or more, preferably 0.5 MDa or more.

According to some embodiments, the at least partially deacetylated glycosaminoglycan is obtained by a method for at least partial deacetylation of a glycosaminoglycan, comprising:

a1) providing a glycosaminoglycan comprising acetyl groups;

a2) allowing the glycosaminoglycan comprising acetyl groups to react with hydroxylamine (NH$_2$OH) or a salt thereof at a temperature of 100° C. or less for 2-200 hours to form an at least partially deacetylated glycosaminoglycan; and a3) recovering the at least partially deacetylated glycosaminoglycan.

EXPERIMENTAL EXAMPLES

The following non-limiting examples will further illustrate the present invention. In these examples, the GAG used is hyaluronic acid, denoted HA and referring to sodium hyaluronate.

Analytical Test Methods

Gel Content (GelC)

The GelC describes in % the proportion of the total HA that is bound in gel form. Gel content is defined as the amount of HA in a sample that does not pass through a 0.22 µm filter. GelC is calculated from the amount of HA that is collected in the filtrate and is given in percent of the total amount of HA in the gel sample.

MoD (Degree of Modification)

MoD describes the molar amount of bound cross-linking agent(s) relative to the total number of repeating HA disaccharide units. This measure does not distinguish between mono-linked and actually cross-linked cross-linking agent(s), i.e. all cross-linking agent(s) that is bound to HA via at least one covalent bond is included. For instance, a MoD of 1% for a HA gel cross-linked with BDDE means that there is 1 bound (monolinked or cross-linked) molecule of BDDE per 100 disaccharide units in the HA gel.

MoD may be determined using NMR spectroscopy on enzymatically degraded gel product. Soluble HA, residual (non-bound) cross-linking agent(s) and derivatives thereof are washed away prior to the degradation of the gel by filtration on a 0.22 µm filter. The gel product is degraded at 37° C. by enzymatic treatment using Chondroitinase AC from *Arthrobacter aurescens*. The degraded gel product is subjected to NMR spectroscopy by recording one-dimensional $^1$H NMR spectra on a 400 MHz spectrometer, equipped with a standard 5 mm probe.

The NMR spectra may be evaluated by integration of the signal at $\delta_H$ 1.6 ppm, which origins from four protons in the linked BDDE molecule, and the signals at δH 2.0 ppm, which is from the three protons in the CH$_3$ groups on the N-acetylglucosamine residues of the HA disaccharides. The ratio between the integrals for these two signals is proportional to the ratio between the molar amount of bound BDDE and disaccharides after correction for the number of protons responsible for each signal, hence giving MoD.

$$MoD = \frac{n_{bound\,crosslinking\,agent}}{n_{disaccharide\,units}}$$

Charging Ratio

Another quantity for measuring the degree of cross-linking is the charging ratio, i.e. the ratio between the number of crosslinking agents added to the reaction vessel and the total number of disaccharide units added to the reaction vessel when performing the cross-linking reaction. The charging ratio may not be the same as the MoD, since the crosslinking reaction may be incomplete, i.e. all cross-linkers may not have reacted to form crosslinks.

Swelling Factor (SwF)

The strength or density of the gel network after cross-linking can be estimated/determined e.g. by allowing the gel to absorb water or saline to equilibrium. As a result of chain breaks during degradation of the gel, the network becomes weaker and less dense, which can be detected by the increasing swelling factor (SwF). The SwF is measured according to the following protocol: About 1 g of gel product is weighed into a measuring glass. Saline is added, the gel is thoroughly dispersed and allowed to absorb water until equilibrium. After sedimentation, the volume of the saturated gel is read. The ratio final volume to initial volume is denoted Swelling Factor (SwF).

Example 1—General Process Outline for Producing a Combination Gel

Figure 1:
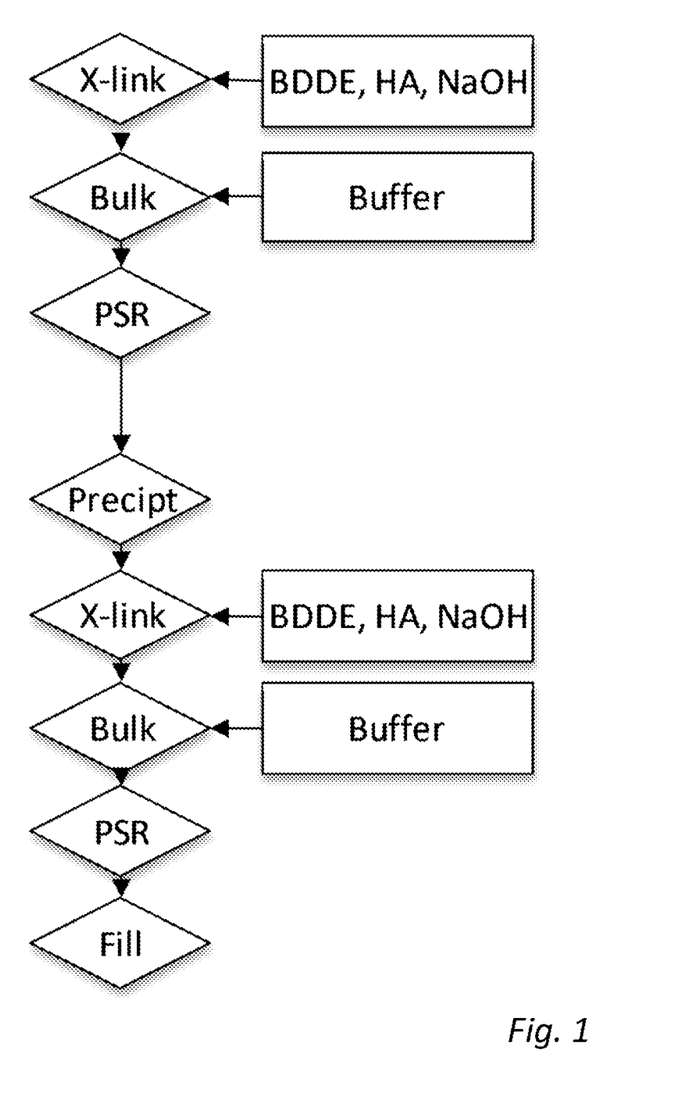
FIG. 1 shows a graphical outline of an embodiments of the method of the present disclosure. PSR=particle size reduction

An embodiment of a method for producing an injectable gel product crosslinked with BDDE is graphically outlined in FIG. 1. In the process, the bulk is precipitated and dried after the first particle size reduction step (PSR). The dry, crosslinked, gel powder is subsequently mixed with HA, BDDE and NaOH for a second crosslinking, where the previously crosslinked gel particles become embedded into a second gel material. The second material is then subjected to the same process steps as in the normal process. The particles from the first PSR are smaller than those from the second PSR, to allow room for the inner gel into the outer gel.

The first and second cross-linking are typically carried out at a temperature of 10-75 degrees centigrade, e.g. 10-40 degrees centigrade, such as 10-35 degrees centigrade or 10-30 degrees centigrade but it is preferred that the step is carried out at 15-35 degrees centigrade, such as 15-30 degrees centigrade, and especially at room temperature, e.g. 20-25 degrees centigrade. Preferred temperature ranges are 10-50 degrees centigrade, such as 18-40 degrees centigrade.

The reaction time is suitably in the range of 2-40 h, such as 4-36 h. A longer reaction time than 2 h is useful for reproducibility, especially at larger scale. Longer reaction time than 40 h yields a gel with lower gel strength or may even disrupt the gel entirely. The reaction time is preferably in the range of 8-30 h, such as 12-24 h, e.g. 16-24 h.

As an example, the cross-linking step may be performed at 15-35 degrees centigrade for 2-40 h, such as at room temperature for 16-24 h.

Figure 4:
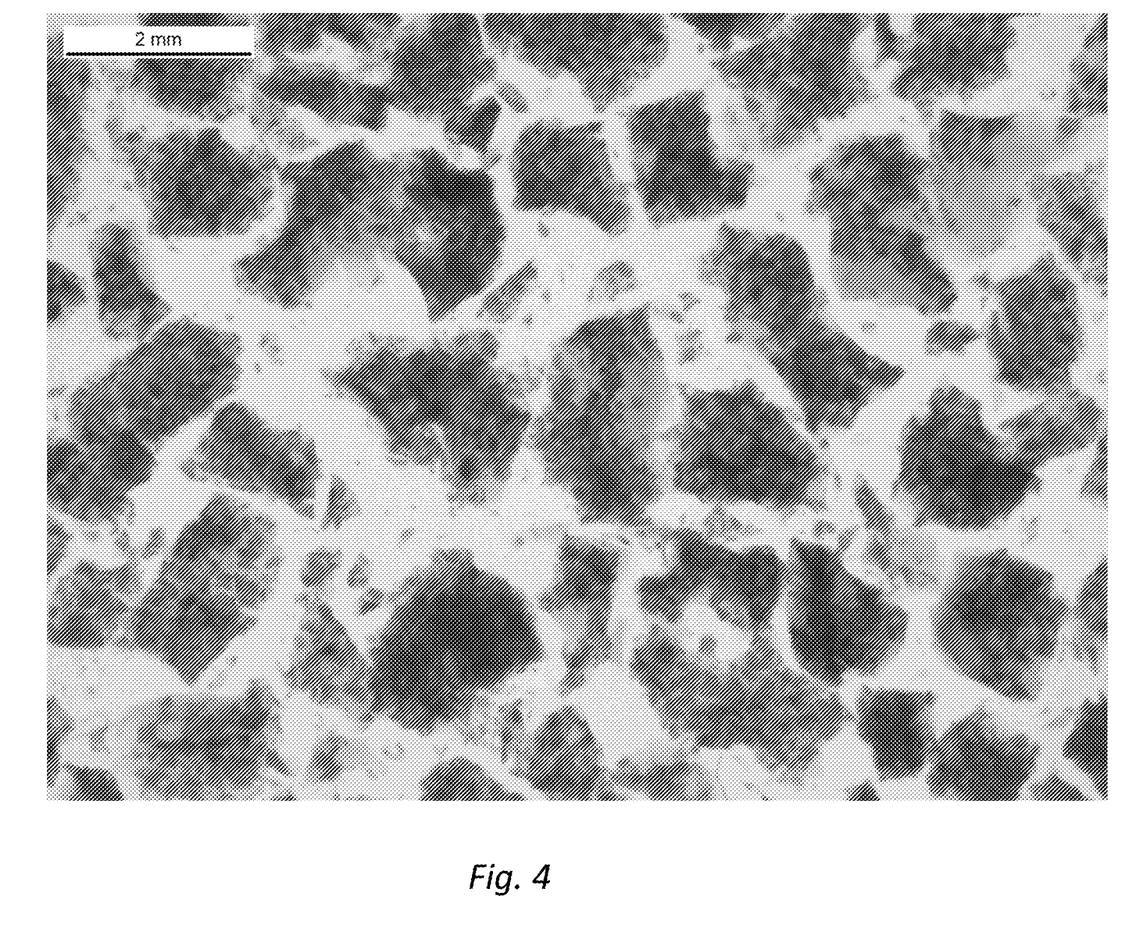
FIG. 4 shows gel particles with embedded gel particles at a magnification of 10×.

FIG. 4 shows a microscope image at a magnification of 10× of gel particles obtained by the method of the present disclosure, with smaller particles embedded in the large particles.

Example 2—Preparation of One-Component Gel

A one-component gel was prepared as follows: 100 g HA (Mw 1 MDa) was mixed and allowed to react with 200 g NaOH 3% w/w and 1.8 g BDDE—resulting in a charging ratio of 0.036. After crosslinking, the gel was neutralized and heat-treated to inactivate any residual crosslinker. Particle size reduction (PSR) was done using an 80 μm mesh. The gel was precipitated in EtOH to obtain a gel powder, which was washed and dried.

Example 3—Preparation of One-Component Gel

Performed as example 2, but using 30 g HA, 73.5 g NaOH 2.5% w/w and 0.22 g BDDE—resulting in a charging ratio of 0.015.

Example 4—Preparation of Two-Component Gel

A two-component gel was prepared as follows: 5 g of the gel powder from example 2 was mixed and allowed to react with 5 g HA (mw 1 MDa), 45.5 g NaOH 1.33% w/w and 90 mg BDDE—resulting in a charging ratio of 0.036. The PSR from example 2 was repeated, but using a 315 μm mesh. The two-component gel powder was hydrated to a final concentration of 20 mg/ml in phosphate buffer and autoclaved. The gel was subjected to 90° C., and the gel content was measured at 16 h intervals (se FIG. 2). Thus, in Example 4, the charging ratio in both the first and second crosslinking reaction was 0.036.

Example 5—Preparation of Two-Component Gel

Figure 2:
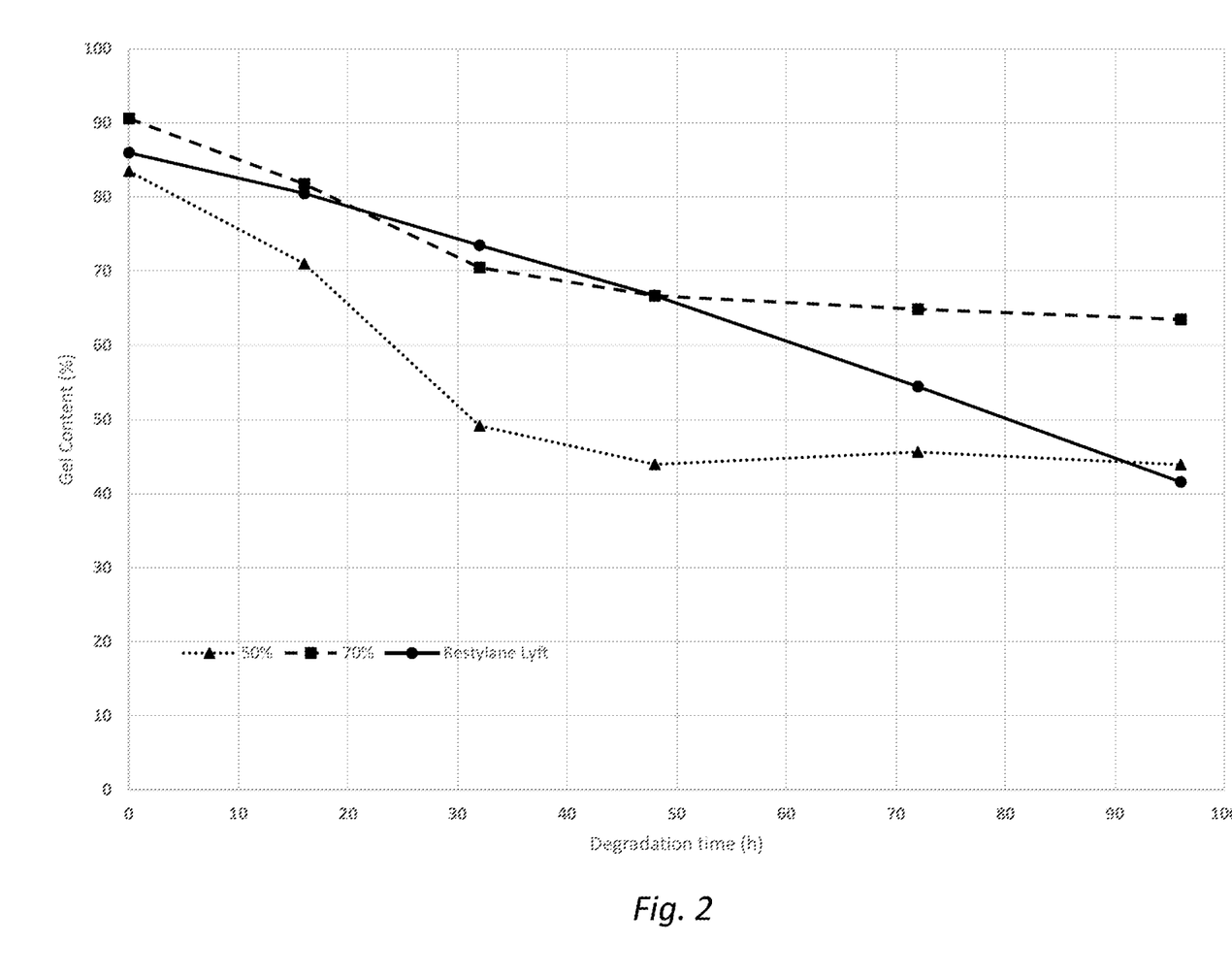
FIG. 2 shows results from degradation tests.

Performed as example 4, but with 7 g of the gel powder from example 2 and 3 g HA, resulting in a charging ratio of 0.043. The gel was subjected to 90° C., and the gel content was measured at 16 h intervals (FIG. 2). Restylane Lyft (from Galderma) was used as a reference. Thus, in Example 5, the charging ratio was 0.036 in the first crosslinking reaction and 0.043 in the second crosslinking reaction.

The gels of Examples 4 and 5 had the following initial characteristics:

| Sample | Dry weight content of inner gel | GelC % | [HA] (mg/ml) |
| --- | --- | --- | --- |
| Example 4 | 50% | 83 | 20 |
| Example 5 | 70% | 91 | 19 |
| Restylane Lyft | — | 86 | 20 |

As seen in FIG. 2, the 70% combination gel degrades until the outer gel is gone, and then levels out at about 70% remaining gel which is degraded at a lower rate. The same type of behaviour was observed with the 50% combination gel, but this gel levels out at 50%. The reference gel, containing only a single gel type, is degraded at a more constant rate. These results clearly demonstrate the combination gel concept, i.e. a combination gel having an outer gel that degrades first before the inner gel starts to degrade. The same type of behaviour is expected in vivo.

Example 6—Preparation of Two-Component Gel

Figure 3:
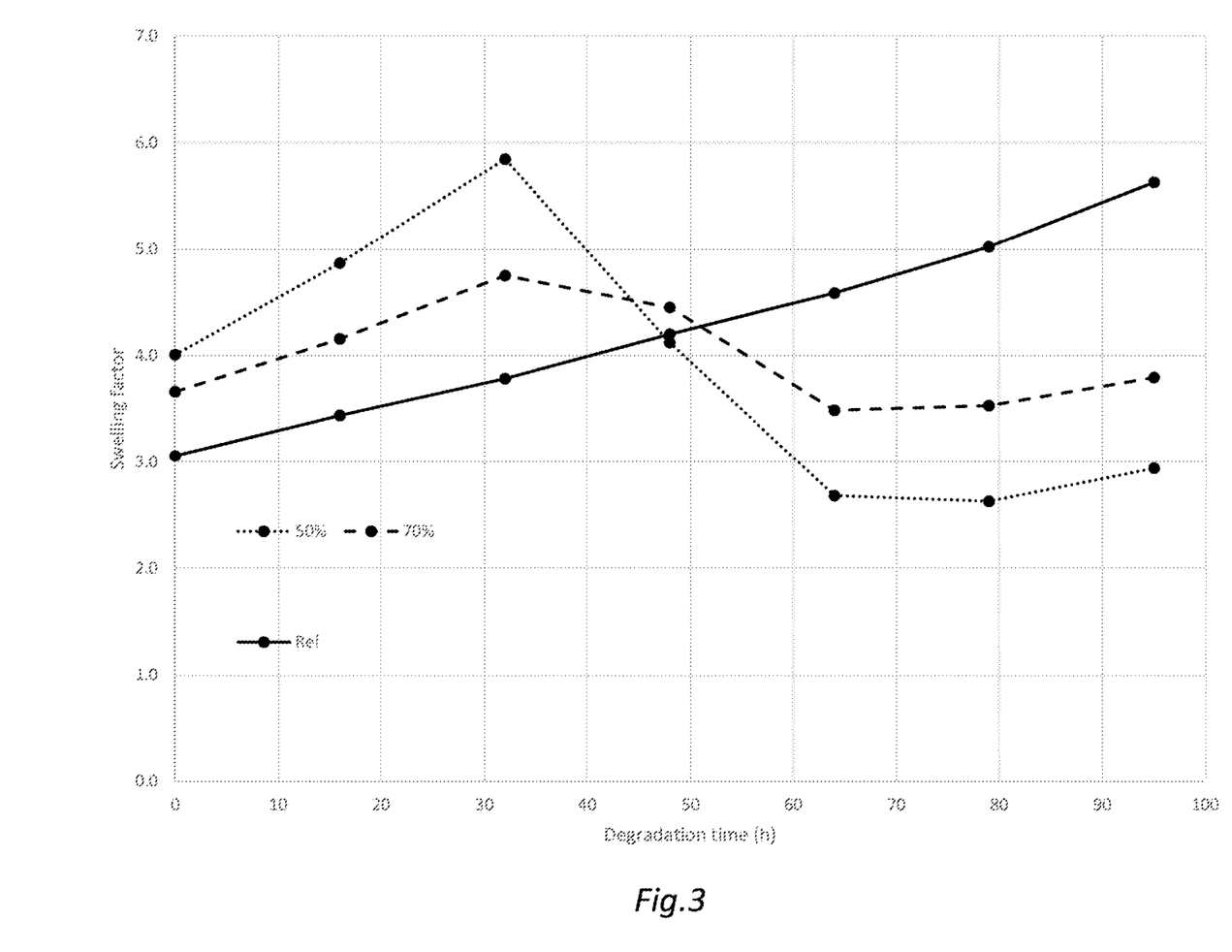
FIG. 3 shows results from degradation tests.
Figure 5:
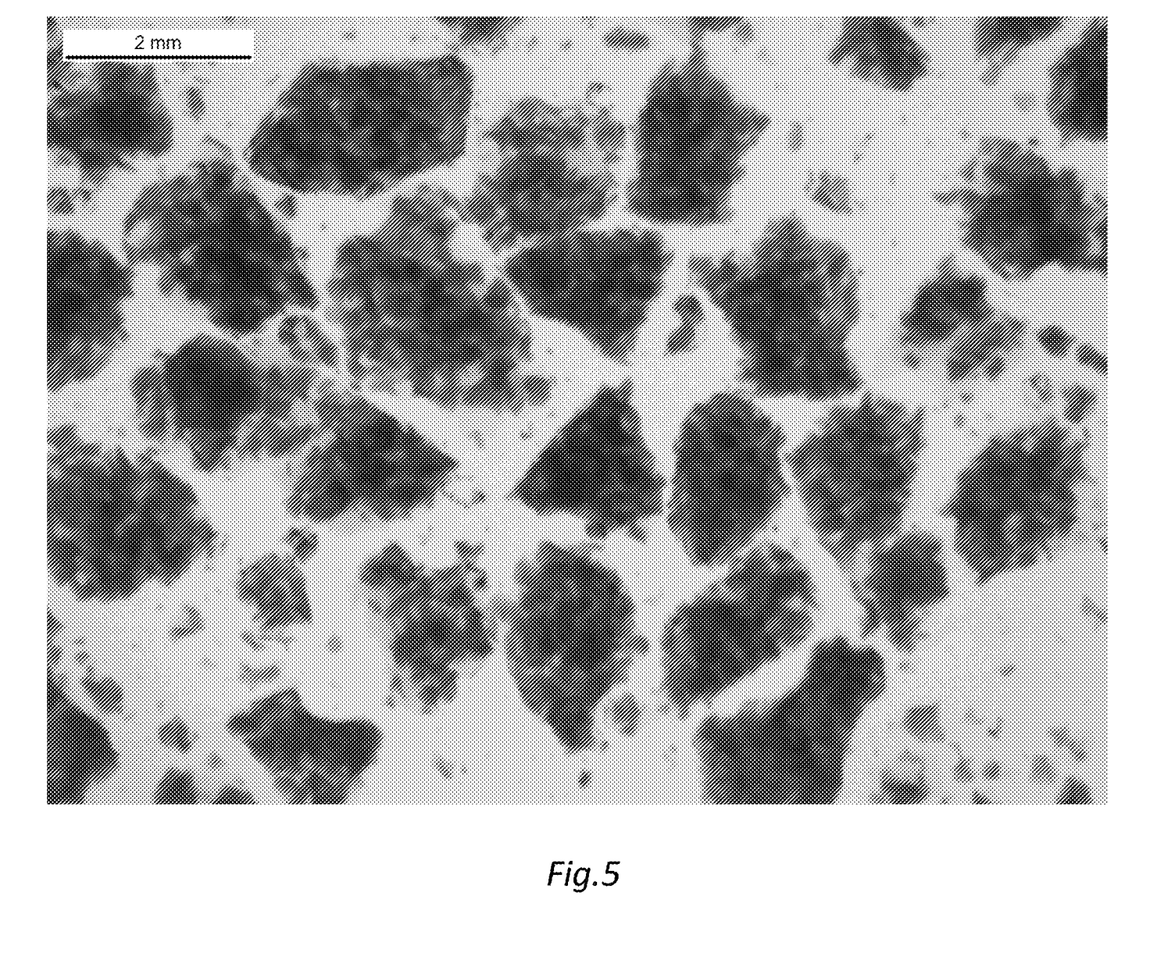
FIG. 5 shows a microscope image of gel particles obtained in Example 6 at a magnification of 10×.

Performed as example 4, but with 2.5 g of the gel powder from example 3 and 2.5 g HA (Mw 1 MDa), 15 g NAOH 2% w/w and 35 mg BDDE, resulting in a charging ratio of 0.022. The gel was subjected to 90° C., and the swelling factor was measured at 16 h intervals (FIG. 3). As a reference, gel powder from example 3 was crosslinked a second time to correspond to the inner gel of examples 6 and 7. FIG. 5 shows a microscope image of gel particles obtained in Example 6 at a magnification of 10×.

Thus, in Example 6, the charging ratio was 0.015 in the first crosslinking reaction and 0.022 in the second crosslinking reaction.

Example 7—Preparation of Two-Component Gel

Performed as example 6, but with 3.5 g of the gel powder from example 3 and 1.5 g HA, resulting in a charging ratio of 0.025. The gel was subjected to 90° C., and the swelling factor was measured at 16 h intervals (FIG. 3). Thus, in Example 7, the charging ratio was 0.015 in the first crosslinking reaction and 0.025 in the second crosslinking reaction.

The gels of Examples 6 and 7 had the following initial characteristics:

| Sample | Dry weight content of inner gel | SwF | [HA] (mg/ml) | GelC % |
| --- | --- | --- | --- | --- |
| Example 6 | 50% | 4.0 | 20 | 93 |
| Example 7 | 70% | 3.7 | 20 | 94 |
| Ref | — | 3.1 | 20 | 96 |

The 50% combination gel increases its swelling more than the other gels since this gel comprises a large portion of the softer outer gel, that mostly contributes to the swelling. After a certain period of time (about 40 hours for the 50% combination gel), the outer gel is gone and only the firmer inner gel may contribute to the swelling. This gives a drop in measured SwF, that then slowly rises again due to swelling of the inner gel. The 70% combination gel shows a similar, but less distinct behaviour, since it contains a lower amount of the outer gel. The gel having only an inner gel (single gel) shows a more constant increase in swelling behaviour. Thus, the inner gel will, after degradation of the outer gel, display a swelling factor similar to that of the initial combination gel.

The below Table summarizes the charging ratios used for preparing the two-component gels in experimental Examples 4-7 above:

| Sample | Charging ratio 1st crosslinking reaction | Charging ratio 2nd crosslinking reaction |
| --- | --- | --- |
| Example 4 | 0.036 | 0.036 |
| Example 5 | 0.036 | 0.043 |
| Example 6 | 0.015 | 0.022 |
| Example 7 | 0.015 | 0.025 |

Further, performing the first and second crosslinking reactions having the charging ratios according to the Table above resulted in the below degree of modification (MoD) for the inner and outer gels in the prepared two-component gels in experimental Examples 4-7:

| Sample | MoD inner gel in the two-component gel (%) | MoD outer gel in the two-component gel (%) |
| --- | --- | --- |
| Example 4 | 3.9 | 1.1 |
| Example 5 | 3.9 | 1.1 |

-continued

| Sample | MoD inner gel in the two-component gel (%) | MoD outer gel in the two-component gel (%) |
|---|---|---|
| Example 6 | 2.2 | 1.0 |
| Example 7 | 2.2 | 1.0 |

Thus, the MoD of the inner gels in all Examples are higher than the MoD of the outer gels, which is due to crosslinkers diffusing into the inner gel during the second crosslinking reaction to crosslink this gel further, thereby increasing the MoD of the inner gel during the second crosslinking step.

Example 8—Preparation of One-Component Gels Crosslinked with Amide Bonds

Gels were also prepared using crosslinking with amide bonds, in which hyaluronic acid (HA), DATH (diaminotrehalose) and DMTMM (4-(4,6-dimethoxy-1,3,5-triazin-2-yl)-4-methylmorpholinium chloride) are mixed and allowed to react. DMTMM functions as a coupling agent whereas DATH functions as a crosslinker.

A one-component gel was prepared as follows: HA was mixed and allowed to react with proper amounts of DATH and DMTMM solved in water. After crosslinking, the gel was diluted to 20 mg/g in Saline and heated to 70° C. for about 20 hours. Particle size reduction (PSR) was done using 125 µm mesh. The gel was precipitated in EtOH to obtain a gel powder, which was washed and dried.

Example 9—Preparation of Two-Component Gels Crosslinked with Amide Bonds

Dry, crosslinked, gel powder of HA crosslinked with amide bonds prepared as in Example 8 was subsequently mixed and allowed to react with proper amounts of HA, DATH and DMTMM solved in water for a second crosslinking, where the previously crosslinked gel particles became embedded into a second gel material.

After the second crosslinking, the gel was diluted to 20 mg/g in Saline and heated to 70° C. for about 20 hours. Particle size reduction (PSR) was done using 315 µm mesh. The gel was precipitated in EtOH to obtain a gel powder, which was washed and dried. The two-component gel powder was hydrated to a final concentration of 20 mg/ml in phosphate buffer and autoclaved.

Figure 6:
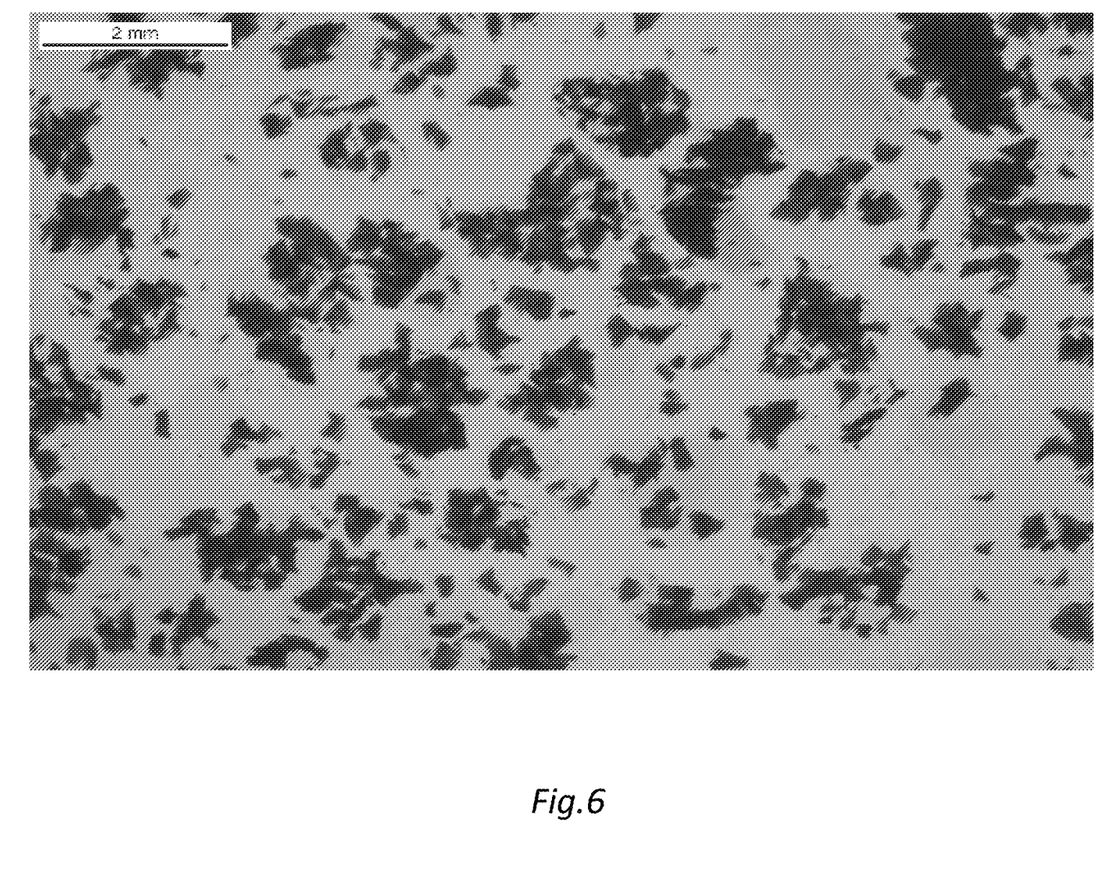
FIG. 6 shows a microscope image of gel particles obtained in Example 9.

A micrograph of the prepared two-component gel from Example 9 is shown in FIG. 6.

Gel characteristics of the gels crosslinked with amide bonds are shown in the below Table:

| Example | HA-conc (mg/g) | GelC (%) | SwF (ml/g) | G' (Pa) | G" (Pa) | Tanδ |
|---|---|---|---|---|---|---|
| 8 | 20 | 96 | 2.9 | 1261 | 115 | 0.09 |
| 9 | 20 | 82 | 4.4 | 288 | 36 | 0.12 |

The person skilled in the art realizes that the present invention by no means is limited to the preferred embodiments described above. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A method of producing an injectable gel product, comprising:
   (a) cross-linking a first glycosaminoglycan (GAG) with a first crosslinking agent at a first charging ratio of crosslinking agent to disaccharide unit below 0.15 to produce a gel;
   (b) preparing particles of the gel;
   (c) mixing the GAG gel particles with a second GAG to provide a mixture;
   (d) cross-linking the second GAG with a second cross-linking agent to obtain a gel having a first, inner phase of the cross-linked GAG gel particles embedded in a second, outer phase comprising the second GAG, and
   (e) preparing injectable particles of the gel from (d), each such particle containing a plurality of the cross-linked GAG gel particles of the first, inner phase;
   wherein the inner phase, the outer phase, or both the inner phase and the outer phase are crosslinked via one or more polyfunctional cross-linking agent selected from 1,4-butanediol diglycidyl ether (BDDE), 1,2-ethanediol diglycidyl ether (EDDE) and diepoxyoctane.

2. The method according to claim 1, wherein the one or more polyfunctional cross-linking agent is BDDE.

3. The method according to claim 1, wherein both the first GAG and the second GAG are covalently crosslinked via a polyfunctional cross-linking agent selected from 1,4-butanediol diglycidyl ether (BDDE), 1,2-ethanediol diglycidyl ether (EDDE) and diepoxyoctane.

4. The method according to claim 1, wherein the first GAG is covalently crosslinked via a polyfunctional cross-linking agent selected from 1,4-butanediol diglycidyl ether (BDDE), 1,2-ethanediol diglycidyl ether (EDDE) and diepoxyoctane.

5. The method according to claim 4, wherein the second GAG is covalently crosslinked via crosslinks comprising a spacer group selected from the group consisting of di-, tri-, tetra-, and oligosaccharides.

6. The method according to claim 5, wherein the spacer group is a hyaluronic acid tetrasaccharide, hyaluronic acid hexasaccharide, trehalose, lactose, maltose, sucrose, cellobiose or raffinose residue.

7. The method according to claim 1, wherein the second GAG is covalently crosslinked via a polyfunctional cross-linking agent selected from 1,4-butanediol diglycidyl ether (BDDE), 1,2-ethanediol diglycidyl ether (EDDE) and diepoxyoctane.

8. The method according to claim 7, wherein the first GAG is covalently crosslinked via crosslinks comprising a spacer group selected from the group consisting of di-, tri-, tetra-, and oligosaccharides.

9. The method according to claim 8, wherein the spacer group is a hyaluronic acid tetrasaccharide, hyaluronic acid hexasaccharide, trehalose, lactose, maltose, sucrose, cellobiose or raffinose residue.

10. The method according to claim 1, wherein the second GAG is cross-linked with the second crosslinking agent at a second charging ratio of crosslinking agent to disaccharide unit that is less than the first charging ratio.

11. The method according to claim 10, wherein the second charging ratio is less than 0.05.

12. The method according to claim 1, wherein the cross-linking (d) further comprises cross-linking between the gels of the first, inner phase and the second, outer phase.

13. The method according to claim 1, wherein the GAG gel particles and the second GAG are both in a dry state when mixed.

14. The method according to claim 1, wherein the preparation of particles comprise precipitating and drying.

15. The method according to claim 1, wherein the mixture (c) comprises at least 50% by dry weight of the GAG gel particles.

16. The method according to claim 1, wherein the cross-linking (a) and/or (b) results in ether bonds.

17. The method according to claim 1, wherein the GAG is hyaluronic acid.

18. An injectable gel product comprising a first, inner phase of a plurality of cross-linked glycosaminoglycan (GAG) gel particles embedded in a second, outer phase of a cross-linked GAG gel,
wherein the second, outer phase is in the form of particles,
wherein the gel of the first, inner phase has a Degree of Modification (MoD) of 0.15 or lower,
wherein the gel of the second, outer phase has a MoD that is lower than the MoD of the gel of the first, inner phase, and
wherein the MoD is the molar amount of bound cross-linking agent(s) relative to the total molar amount of repeating GAG disaccharide units;
wherein the inner phase, the outer phase, or both the inner phase and the outer phase are crosslinked via one or more polyfunctional cross-linking agent selected from 1,4-butanediol diglycidyl ether (BDDE), 1,2-ethanediol diglycidyl ether (EDDE) and diepoxyoctane.

19. The injectable gel product according to claim 18, wherein the one or more polyfunctional cross-linking agent is BDDE.

20. The injectable gel product according to claim 18, wherein each of the plurality of crosslinked GAG gel particles in the first, inner phase and the plurality of crosslinked GAG gel particles in the second, outer phase are independently covalently crosslinked via a polyfunctional cross-linking agent selected from 1,4-butanediol diglycidyl ether (BDDE), 1,2-ethanediol diglycidyl ether (EDDE) and diepoxyoctane.

21. The injectable gel product according to claim 18, wherein the plurality of crosslinked GAG gel particles in the first, inner phase are covalently crosslinked via a polyfunctional cross-linking agent selected from 1,4-butanediol diglycidyl ether (BDDE), 1,2-ethanediol diglycidyl ether (EDDE) and diepoxyoctane.

22. The injectable gel product according to claim 21, wherein the plurality of crosslinked GAG gel particles in the second, outer phase are independently covalently cross-linked via crosslinks comprising a spacer group selected from the group consisting of di-, tri-, tetra-, and oligosaccharides.

23. The injectable gel product according to claim 22, wherein the spacer group is a hyaluronic acid tetrasaccharide, hyaluronic acid hexasaccharide, trehalose, lactose, maltose, sucrose, cellobiose or raffinose residue.

24. The injectable gel product according to claim 18, wherein the plurality of crosslinked GAG gel particles in the second, outer phase are covalently crosslinked via a polyfunctional cross-linking agent selected from 1,4-butanediol diglycidyl ether (BDDE), 1,2-ethanediol diglycidyl ether (EDDE) and diepoxyoctane.

25. The injectable gel product according to claim 24, wherein the plurality of crosslinked GAG gel particles in the first, inner phase are independently covalently crosslinked via crosslinks comprising a spacer group selected from the group consisting of di-, tri-, tetra-, and oligosaccharides.

26. The injectable gel product according to claim 25, wherein the spacer group is a hyaluronic acid tetrasaccharide, hyaluronic acid hexasaccharide, trehalose, lactose, maltose, sucrose, cellobiose or raffinose residue.

27. The injectable gel product according to claim 18, wherein the MoD of the gel of the second, outer phase is 0.10 or lower.

28. The injectable gel product according to claim 18, wherein the gel of the second, outer phase has a Swelling factor (SwF) above 3.0.

29. The injectable gel product according to claim 18, wherein the gels of the first, inner phase and the second, outer phase are cross-linked to each other.

30. The injectable gel product according to claim 18, wherein the particles of the second, outer phase have a particle size at least three times the size of an inner particle size.

31. The injectable gel product according to claim 18, wherein the cross-linked GAG of the first, inner phase have a dry weight content of that is at least 50% of the total dry weight content of GAGs in the inner and outer phase.

32. The injectable gel product according to claim 18, wherein the GAG is hyaluronic acid.

33. The injectable gel product according to claim 18, wherein the cross-linking is with ether bonds.

34. The injectable gel product according to claim 18, further comprising a buffering agent.

35. A pre-filled syringe, comprising the injectable gel product according to claim 18.

* * * * *